(12) United States Patent
Grajcar et al.

(10) Patent No.: US 10,104,875 B2
(45) Date of Patent: Oct. 23, 2018

(54) SYSTEM AND METHOD OF ENHANCING REPRODUCTION IN AVIAN

(71) Applicant: Once Innovations, Inc., Plymouth, MN (US)

(72) Inventors: Zdenko Grajcar, Orono, MN (US); John Lilly, Minneapolis, MN (US); Kevin Payne, Brecksville, OH (US)

(73) Assignee: Once Innovations, Inc., Plymouth, MN (US)

(*) Notice: Subject to any disclaimer, the term of this patent is extended or adjusted under 35 U.S.C. 154(b) by 0 days.

(21) Appl. No.: 15/811,794

(22) Filed: Nov. 14, 2017

(65) Prior Publication Data

US 2018/0125040 A1     May 10, 2018

Related U.S. Application Data

(63) Continuation of application No. 15/503,738, filed as application No. PCT/US2015/046641 on Aug. 25, 2015, now Pat. No. 9,844,210.
(Continued)

(51) Int. Cl.
*A01K 45/00* (2006.01)
*A01K 29/00* (2006.01)
(Continued)

(52) U.S. Cl.
CPC ............ *A01K 45/007* (2013.01); *A01K 31/22* (2013.01); *A01K 67/02* (2013.01); *A61D 19/02* (2013.01); *H05B 33/0845* (2013.01); *H05B 33/0857* (2013.01); *H05B 37/0272* (2013.01); *H05B 37/0281* (2013.01); *F21V 3/00* (2013.01); *F21V 29/77* (2015.01); *F21V 29/87* (2015.01); *F21V 31/005* (2013.01); *F21Y 2115/10* (2016.08)

(58) Field of Classification Search
CPC ................................ A01K 29/00; A01K 45/00
USPC ............................ 119/6.8, 174, 437; 800/19
See application file for complete search history.

(56) References Cited

U.S. PATENT DOCUMENTS 4,625,728 A * 12/1986 Schonberg ............... A01G 7/00
                                                                                                   119/6.8
4,872,421 A * 10/1989 Laurent .................. A23K 20/28
                                                                                                   119/174

(Continued)

FOREIGN PATENT DOCUMENTS

CN         101672839 B     11/2012
WO    WO-1984000693 A1     3/1984
(Continued)

OTHER PUBLICATIONS

"U.S. Appl. No. 15/503,738, Notice of Allowance dated Aug. 15, 2017", 9 pgs.

(Continued)

*Primary Examiner* — Yvonne R Abbott-Lewis
(74) *Attorney, Agent, or Firm* — Schwegman Lundberg & Woessner, P.A.

(57) ABSTRACT

Methods and systems of promoting fertilization of eggs of an avian. While inseminating a plurality of avian eggs a spectrum substantially concentrated within a narrow range of wavelength irradiates the plurality of inseminated avian eggs to increase the motility of the sperm to increase the probability of conception of avian from the inseminated eggs.

20 Claims, 7 Drawing Sheets

Related U.S. Application Data

(60) Provisional application No. 62/041,875, filed on Aug. 26, 2014.

(51) Int. Cl.
| | |
|---|---|
| *A01K 67/02* | (2006.01) |
| *A61D 19/02* | (2006.01) |
| *A01K 31/22* | (2006.01) |
| *H05B 33/08* | (2006.01) |
| *H05B 37/02* | (2006.01) |
| *F21V 29/77* | (2015.01) |
| *F21V 29/87* | (2015.01) |
| *F21Y 115/10* | (2016.01) |
| *F21V 3/00* | (2015.01) |
| *F21V 31/00* | (2006.01) |

(56) References Cited

U.S. PATENT DOCUMENTS

| | | | |
|---|---|---|---|
| 5,108,907 A | 4/1992 | Pleass | |
| 5,188,907 A | 2/1993 | Kawahara et al. | |
| 5,900,929 A | 5/1999 | Hebrank et al. | |
| 6,379,939 B1* | 4/2002 | Lubart | A61N 5/0613 435/173.1 |
| 6,573,254 B1* | 6/2003 | Kuenzel | A61D 19/00 514/157 |
| 6,766,767 B2* | 7/2004 | El Halawani | A01K 45/00 119/174 |
| 8,373,363 B2 | 2/2013 | Grajcar | |
| 8,468,976 B2 | 6/2013 | Kakimi et al. | |
| 8,596,804 B2* | 12/2013 | Grajcar | A01K 1/00 119/437 |
| 8,657,463 B2* | 2/2014 | Lichten | F21S 8/063 362/217.05 |
| 9,247,603 B2 | 1/2016 | Grajcar et al. | |
| 9,700,019 B2* | 7/2017 | Grajcar | A01K 29/00 |
| 9,709,228 B2* | 7/2017 | Grajcar | F21S 8/006 |
| 9,844,210 B2 | 12/2017 | Grajcar et al. | |
| 2010/0294205 A1 | 11/2010 | Kakimi et al. | |
| 2010/0310552 A1 | 12/2010 | Rapp et al. | |
| 2011/0101883 A1 | 5/2011 | Grajcar | |
| 2011/0210678 A1 | 9/2011 | Grajcar | |
| 2012/0002408 A1 | 1/2012 | Lichten et al. | |
| 2013/0016506 A1 | 1/2013 | Odom, Jr. | |
| 2014/0252340 A1 | 9/2014 | Wang | |
| 2015/0069932 A1 | 3/2015 | Grajcar | |
| 2015/0247631 A1 | 9/2015 | Grajcar et al. | |
| 2015/0273235 A1 | 10/2015 | Grajcar | |
| 2016/0165698 A1 | 6/2016 | Grajcar | |
| 2017/0273281 A1 | 9/2017 | Grajcar et al. | |
| 2017/0290124 A1 | 10/2017 | Grajcar | |

FOREIGN PATENT DOCUMENTS

| | | |
|---|---|---|
| WO | WO-2015017655 A1 | 2/2015 |
| WO | WO-2016033002 A1 | 3/2016 |

OTHER PUBLICATIONS

"International Application Serial No. PCT/US2015/046641, International Preliminary Report on Patentability dated Mar. 9, 2017", 7 pgs.

"International Application Serial No. PCT/US2015/046641, International Search Report dated Nov. 24, 2015", 2 pgs.

"International Application Serial No. PCT/US2015/046641, Written Opinion dated Nov. 24, 2015", 5 pgs.

"European Application No. 15734927.5 European Search Report dated Sep. 5, 2017", (Sep. 5, 2017), 8 pgs.

"Global Dossier Translation of 1st Office Action dated Apr. 24, 2017 for CN Application No. CN201480047295.6", (Apr. 24, 2017), 9 pgs.

"Global Dossier Translation of 2nd Office Action dated Sep. 26, 2017 for CN Application No. CN201480047295.6", (Sep. 26, 2017), 7 pgs.

"Global Dossier Translation of 3rd Office Action dated Feb. 5, 2018 for CN Application No. CN201480047295.6", (Feb. 5, 2018), 6 pgs.

"International Application Serial No. PCT/US2014/049143, International Preliminary Report on Patentability dated Feb. 11, 2016", (Feb. 11, 2016), 6 pgs.

"International Application Serial No. PCT/US2014/049143, International Search Report dated Nov. 6, 2014", (Nov. 6, 2014), 2 pgs.

"International Application Serial No. PCT/US2015/010407, International Preliminary Report on Patentability dated Jul. 21, 2016", (Nov. 6, 2014), 6 pgs.

"International Application Serial No. PCT/US2015/010407, International Search Report dated Apr. 7, 2015", (Apr. 7, 2015), 2 pgs.

"International Application Serial No. PCT/US2015/010407, Written Opinion dated Apr. 7, 2015", (Apr. 7, 2015), 4 pgs.

"International Application Serial No. PCT/US2017/024679, International Search Report dated Aug. 2, 2017", (Aug. 2, 2017), 4 pgs.

"International Application Serial No. PCT/US2017/024679, Invitation to Pay Additional Fees and Partial Search Report dated Jun. 7, 2017", (Jun. 7, 2012), 2 pgs.

"International Application Serial No. PCT/US2017/024679, Written Opinion dated Aug. 2, 2017", (Aug. 2, 2017), 5 pgs.

Claus, R, et al., "Influence of light and photoperiodicity on pig prolificacy", Journals of Reproduction & Fertility Ltd, (1985), 185-197.

\* cited by examiner

US 10,104,875 B2

SYSTEM AND METHOD OF ENHANCING REPRODUCTION IN AVIAN

CLAIM OF PRIORITY

This application is a continuation application of U.S. patent application Ser. No. 15/503,738, filed Feb. 14, 2017, which application is a U.S. National Stage Filing under 35 U.S.C. 371 from International Patent Application No. PCT/US2015/046641, filed Aug. 25, 2015, published on Mar. 3, 2016 as WO 2016/033002 A1, which application claims the benefit of priority of and is based upon U.S. Provisional Patent Application Ser. No. 62/041,875, filed on Aug. 26, 2014, entitled "System and Method of Enhancing Reproduction in Avian," all of which are hereby incorporated by reference herein in their entireties.

BACKGROUND

Farmed animal reproduction has grown into a multi-million dollar business. For years, in the horse racing field, racing champions have been selected to stud mares in hopes of providing an offspring that will similarly be a champion racer.

In the avian industry the breeding of avian such as turkeys has become its own industry. In particular, as the turkey industry has become more modernized not only have the turkey moved indoor to confinement facilities, a greater emphasis on efficiency within turkey operations has been emphasized. This is true among all facets of turkey production including reproduction.

In the avian field and in particular in the turkey industry artificial insemination is becoming more commonplace in the industry. In particular, semen is collected and then inseminated or delivered with a syringe or plastic straw into the oviduct. This process is expensive and has many drawbacks that have held back more widespread use of this technique. First, once semen is collected its spermatozoal viability can start to decrease after only an hour. Multiple solutions to this issue all have drawbacks, in particular, cooling the sperm to between 2-5° C. in a storage facility and then thawing for insemination can lead to increasing the viability for several hours, though this remains a short period of time. Thus often a semen extender must be added to the semen in addition to being cooled. The cooling storage facilities and extender are expensive and can decrease fertilization.

In addition, sperm production in avian is known to be effected by photoperiods. In particular, sperm production increases during spring time, or when light increases are sensed by the avian. Meanwhile, sperm production decreases during the fall time when photoperiods are decreasing over time.

Overview

A need in the art exists to facilitate successful breeding of avian. In particular, increased chances of successful breeding during all times of the year are desired along with maximizing the chances of conception using the artificial insemination method of reproduction. In addition, improvements regarding the manner and method in which sperm is stored and transported for insemination is needed to reduce costs and increase probabilities of success of successful insemination.

This document relates to avian reproduction. More specifically it relates to stimulating, facilitating and enhancing the avian breeding using a LED lighting system.

Methods and systems for promoting fertilization of eggs of an avian are presented herein. During the insemination of sperm into avian eggs a lighting device is provided to irradiate a plurality of inseminated avian eggs. The eggs are irradiated with a light with a spectrum substantially concentrated within a narrow range of wavelength during a predetermined period of time. The narrow range of wavelength is selected to increase the motility of the sperm within the inseminated avian eggs to increase the probability that the egg becomes fertilized.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
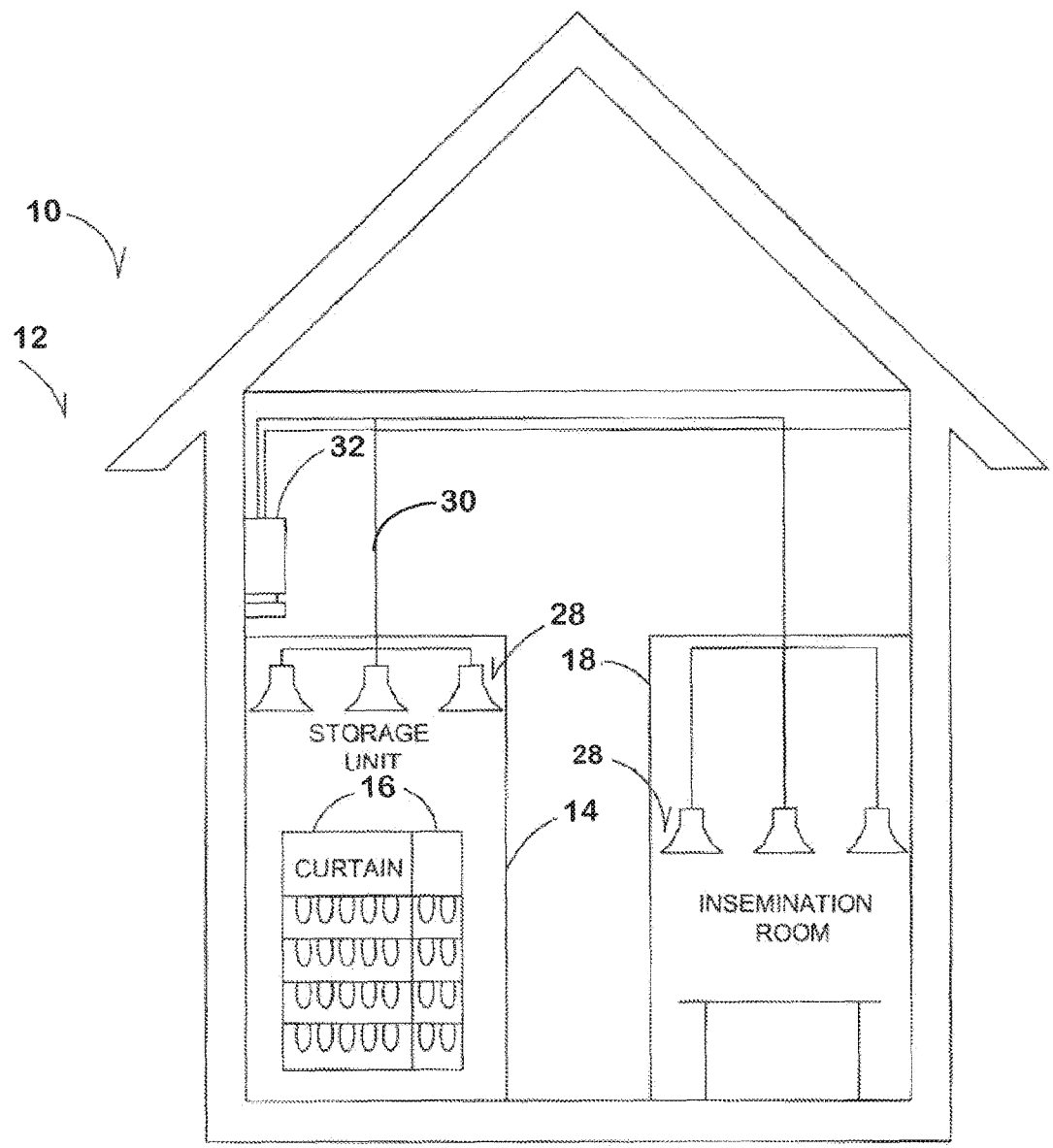
FIG. 1 is a side plan view of an animal confinement facility.
Figure 2:
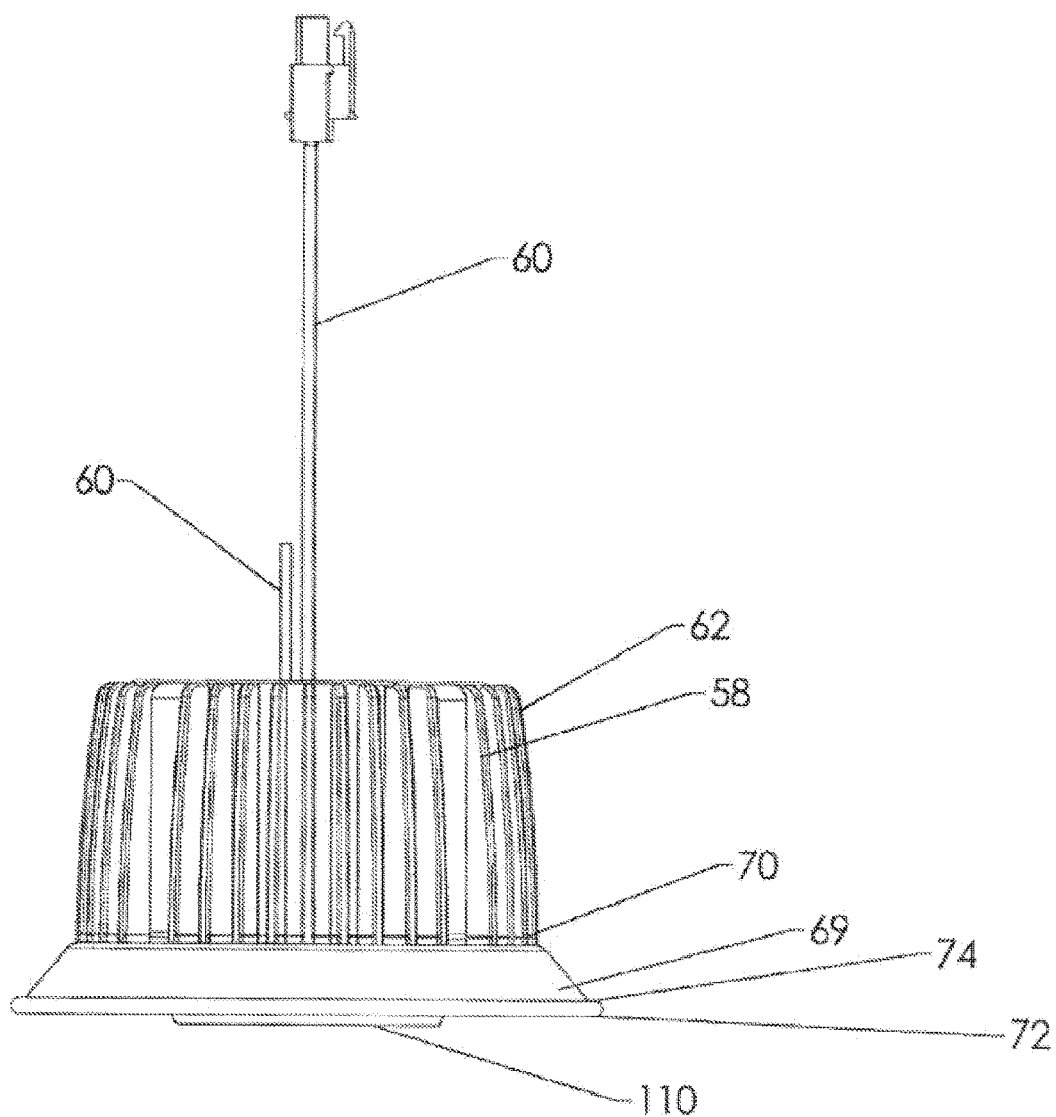
FIG. 2 is a side plan view of a lighting device of a lighting system.
Figure 3:
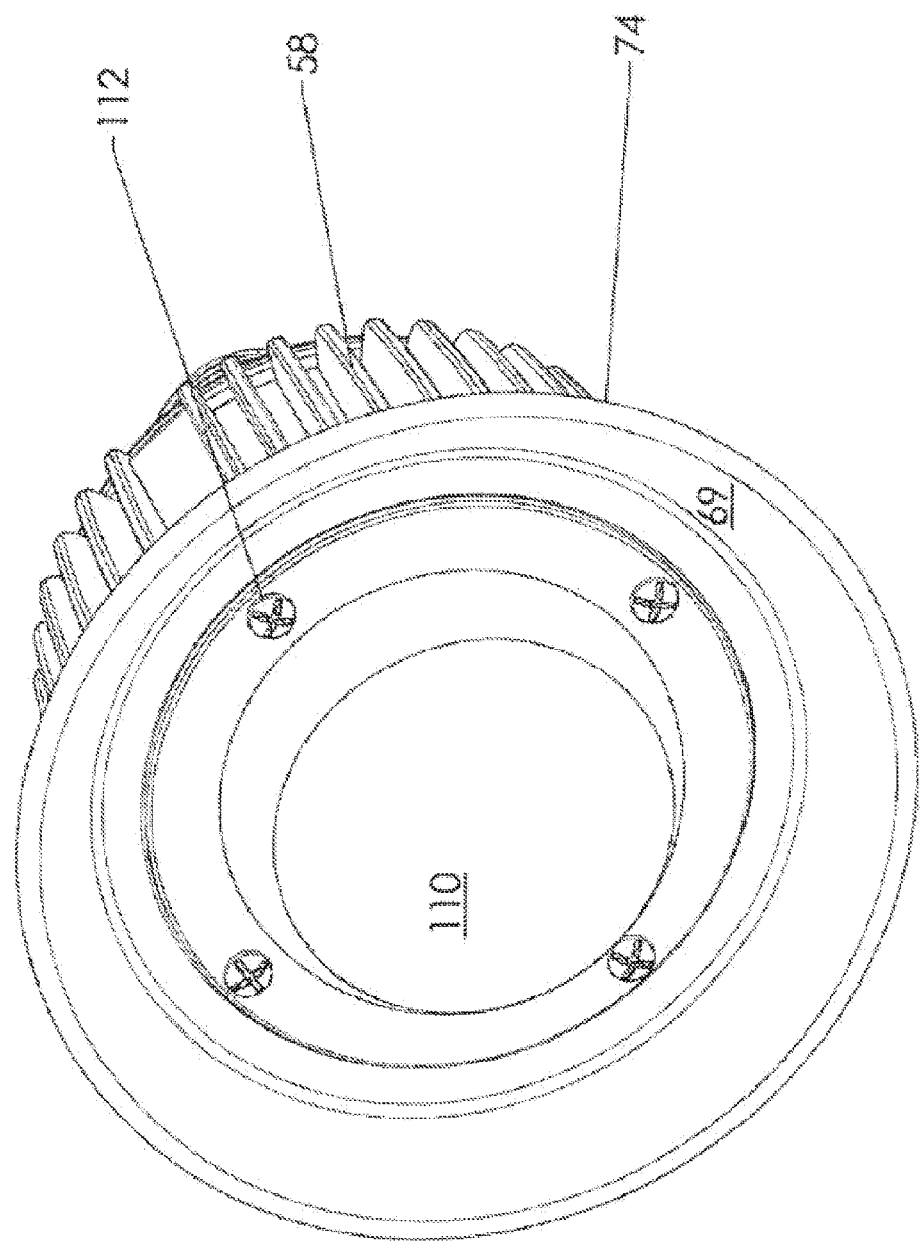
FIG. 3 is a side perspective view of a lighting device of a lighting system.

The figures show an animal confinement facility 10 that in a preferred embodiment is a facility 10 that confines avian, such as an aviary or coup. Still, other animals, including horses, swine, bovine, and other domesticated animals such as sheep and goats, aquatic life including fish and shrimp, or the like could be within the facility without falling outside the scope of this disclosure. In this preferred embodiment the facility 10 is directed toward a turkey breeding facility 10, but again could be any such different facility 10.

The figures show the facility 10 that includes a dwelling 12 such as a barn or coup. The dwelling 12 has at least one storage unit 14 for housing and containing sperm. In one embodiment the storage unit 14 is a cooler having multiple containers 16 or racks for holding the sperm. Also within the facility 10, either in the storage unit 14 or in a different location such as an insemination room 18 the semen is allowed to thaw.

Within the storage unit 14 or the insemination room 18 is a lighting system 28 that in one embodiment includes a plurality of electrical conduit bodies that receive and electrical input from an electrical source 32. The lighting system is of any type, including but not limited to those as previously described in U.S. Pat. No. 8,596,804 entitled "Light Sources Adapted to Spectral Sensitivity of Diurnal Avians and Humans," U.S. Ser. No. 12/916,313 entitled "LED Lighting for Livestock Development," U.S. Prov. Pat. App. 61/861,645 entitled System and Method for Manipulating Psychological and Physiological Characteristics of Swine, all to Grajcar, and all of which are fully incorporated by reference herein. The electrical conduit bodies 30 house wiring that extend to provide an electric excitation signal to different areas in the dwelling 12. In one embodiment the wiring is electrically connected to a socket to receive a lighting assembly 38. In another embodiment the lighting assembly 38 is a tube light or other lighting device connected to or provided adjacent a container 16 holding the sperm.

The lighting assembly 38 includes a base 40 having electrical conducting elements 42 therein that threadably and electrically connects within the socket 36 as is known in the art. The base 40 is either threadably received or compression fit onto a frustroconally shaped body 44 having a hollow interior 46 and a sidewall 48 that extends outwardly and away from a first end 50 having a first diameter to a second end 52 having a second diameter greater than the first diameter. In this manner when waste or feces or water is sprayed on the body 44 the material flows downwardly and off the assembly 38. At the second end is a ring element 54 that is of size and shape to engage a sealing element 56 that in a preferred embodiment is made from an elastic material that expands upon compression. The sealing element 56 is secured between the ring element 54 and heat sink 58 to provide a water tight seal therebetween. In this manner electrical wiring 60 is electrically connected to the conductive body through the body 44 and heat sink within a water tight assembly 38.

In an alternative embodiment a socket 36 is not presented and instead the wiring is directly provided. In this embodiment the body 44 with the base 40 are not provided and instead the electrical wiring 60 disposed through the heat sink is directly or hard wired to the wiring 34 of the conduit to provide a direct electrical connection. The heat sink is then threadably and/or sealing connected to the conduit again to provide a water tight seal to prevent water from being within the interior of the heat sink 58 and being exposed to the electrical wiring 60.

The heat sink 58 in a preferred embodiment is made of a plastic material and has a plurality of fin elements 62 that assist in conveying heat through the sink 58. The heat sink 58 extends from a first end 64 adjacent the conduit bodies 30 that receives the sealing element 56 in one embodiment and is sealed to a conduit body 30 in another to second end 66. The second end 66 is secured to a diffusion element 68 that has a frustroconical shape having a sidewall 69 that extends from a first end 70 outwardly and downwardly from the heat sink 58 to an open second end 72 having a diameter slightly greater than the diameter of the first end 70 and terminating in a lip element 74. By being sloped at an angle and downwardly, again, water, feces and other materials often known to facilities 10 flow off the diffusion element 68, yet the lip element 74 keeps a robust design to withstand the harsh environment.

Figure 4:
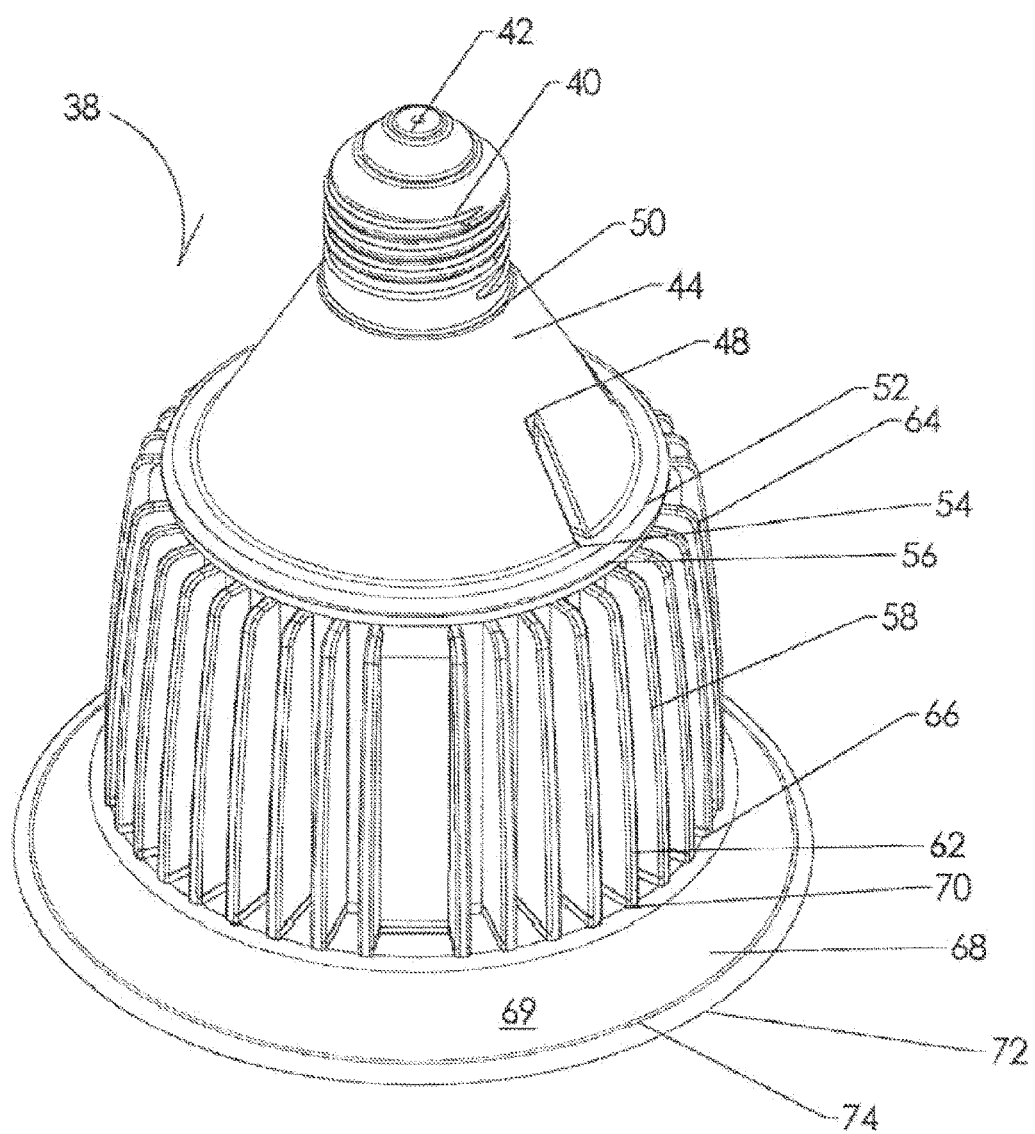
FIG. 4 is a top perspective view of a lighting device of a lighting system.
Figure 5:
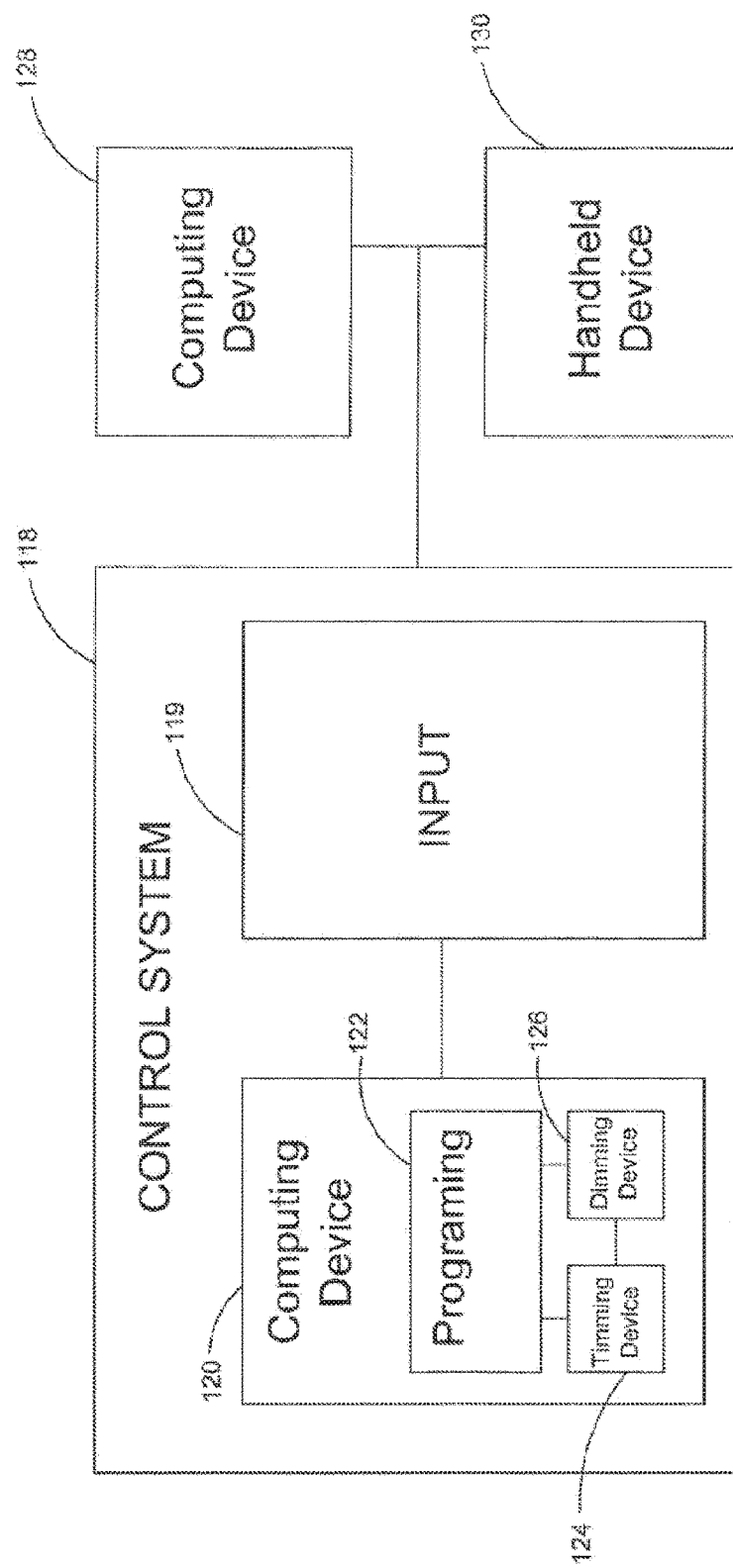
FIG. 5 is a schematic diagram of a control system for a lighting system.
Figure 6:
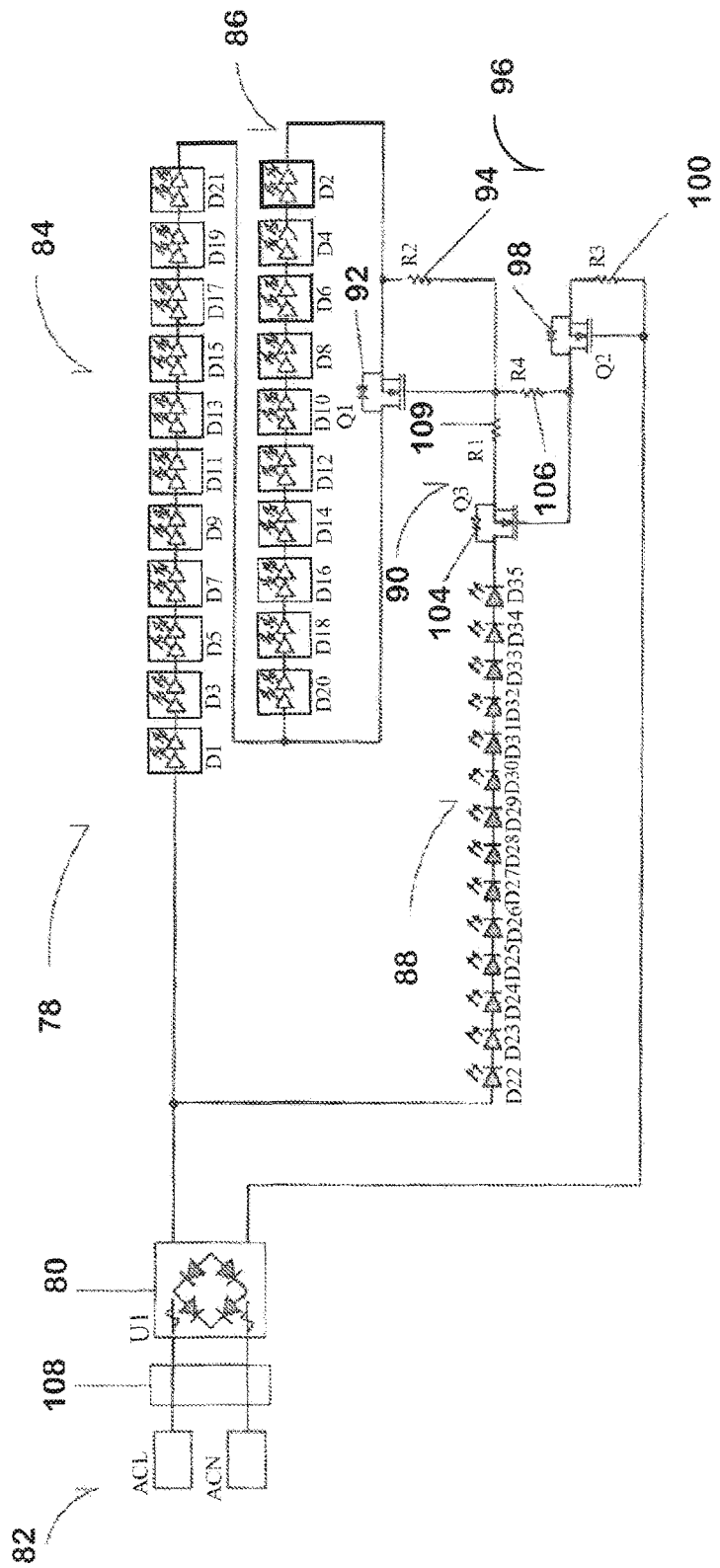
FIG. 6 is a schematic diagram of circuitry of a lighting system.
Figure 7:
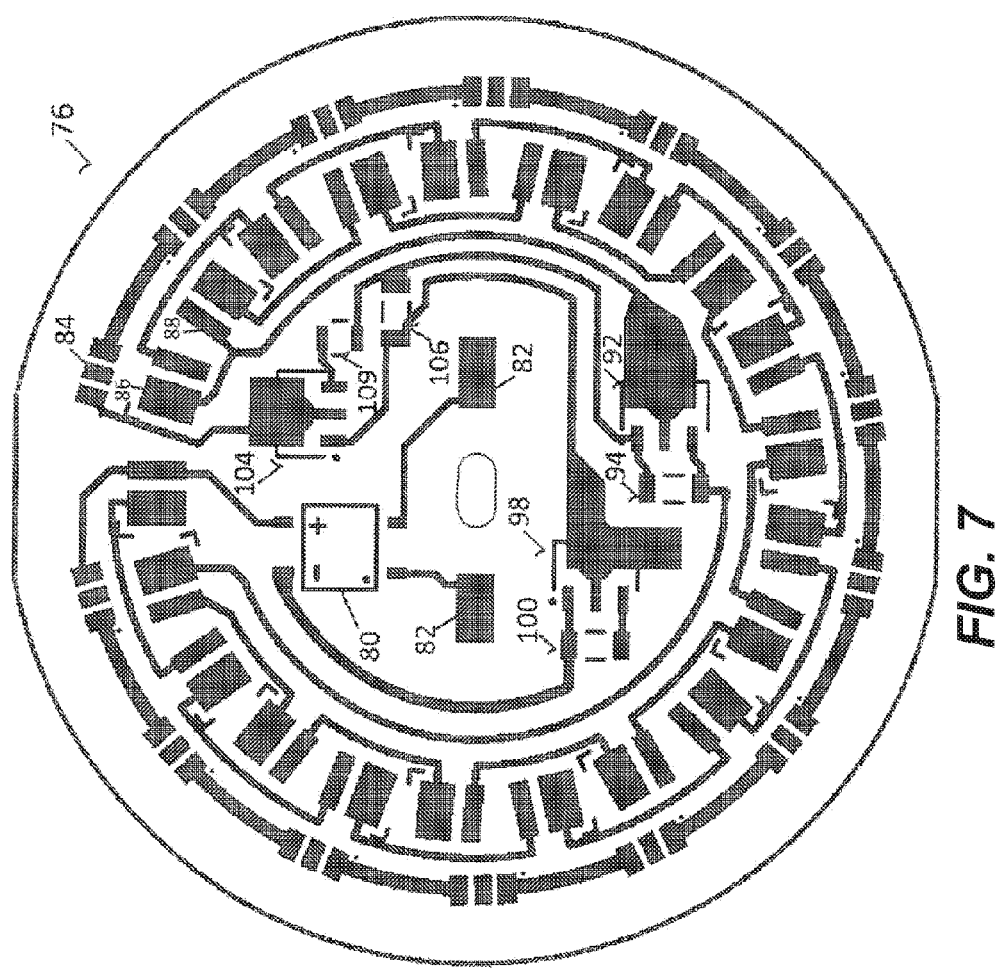
FIG. 7 is a schematic diagram of circuitry of a lighting system.

A substrate 76 is also secured to the second end 66 of the heat sink 58 and in one embodiment has a generally round shape. The substrate also in one embodiment is a printed circuit board. FIG. 4 shows the substrate 76 having driving circuitry 78. The circuitry is similar to that taught in U.S. Pat. No. 8,373,363 entitled Reduction of Harmonic Distortion for LED Loads, by Z. Grajcar and issued on Feb. 12, 2013 and U.S. Patent Application entitled "Color Temperature Shift Control for Dimmable AC LED Lighting," Ser. No. 12/824,215, which was filed by Z. Grajcar on Jun. 27, 2010, the entire contents of each of which are incorporated herein by reference.

The circuitry 78 of the present invention includes a rectifying device 80 that receives current from an AC source 82 and includes a first group of light emitting diodes 84 arranged in series with a second group of light emitting diodes 86, both of which comprise diodes emitting white light. A third group of light emitting diodes 88 comprising diodes emitting red light are presented in parallel to the first and second groups of diodes 84 and 86. Red light emitted is considered any light having a wavelength approximately between 620 nm and 780 nm. Alternatively light emitting diodes having providing blue light, or having a wavelength approximately between 400 nm and 500 nm could be used without falling outside the scope of this invention. A bypass path 90 is presented with a first impedance element 92 that in one embodiment is a transistor. In a preferred embodiment the first impedance element 92 is a depletion MOSFET, though a p-channel MOSFET, n-channel MOSFET or the like can be used without falling outside the scope of this disclosure, even if an additional transistor is required for functionality purposes. A first resistor 94 is also provided to control the flow of current through the first impedance element 92 to provide smooth and continuous current flow.

A second bypass path 96 is also provided with a second impedance element 98 that similarly in one embodiment is a depletion MOSFET. Similar to the first bypass path 90 the second bypass path 96 utilizes a second resistor 100 again to control the impedance element 98. Similarly also, a third bypass path 102 is provided between the third group of light emitting diodes 88 and first and second groups of light emitting diodes 84 and 86. Again, this bypass path 102 utilizes a third impedance element 104 and third resistor 106 to provide similar functionality as the other bypass paths. In this manner when a dimming device 108 is electrically connected to the circuit and the voltage begins dropping, current flow to the first group of diodes 84 drops first, dimming out the first group of white diodes. Then as dimming continues and a threshold current is reached the second group of light emitting diodes 86 begin to dim. Thus, again white light is slowly dimmed and eliminated from the output light. In this manner only the third group of light emitting diodes 88 that are red remain providing light. A supplemental resistor 109 optionally is provided to limit current in the system and to improve efficiencies.

Therefore the assembly dims to produce a red light. Consequently, with a programmable dimming device the lighting assembly 38 can provide a combination of white and red light throughout a 24 hour period to optimize swine characteristics. A lens element 110 is secured to the heat sink 58, diffusion element 68 or both. In one embodiment fastening elements 112 are utilized to provide the connection. In particular the lens element 110 is secured to provide a water tight seal so that water cannot encroach the interior of the assembly 38.

A control system 118 is electronically connected to the lighting assemblies 38. The control system 118 includes an input 119 for actuating a computing system 120 having programming 122 therein associated with a timing device 124. The control system 118 additionally has a dimming device 126 that is electrically connected to the timing device 124 such that the programming 122 at predetermined periods will automatically dim the lighting assemblies 38 to a predetermined light setting. The control system 118 in one embodiment communicates remotely through over the air communications, via Wi-Fi or as is known in the art to provide lighting and dimming information to an individual having a remote computing device 128 or handheld device 130 having the capability to receive such communication. In one embodiment the computing device 128 or handheld device 130 may be used to communicate instructions to the control system 118 such that the control system 118 is remotely controlled by the remote device 128 or 130. Examples of the remote devices include but are not limited to computers, laptop computers, tablets, IPads, smartphones, Blackberry devices, remote controls and the like.

The lighting assemblies 38 are designed as described above such that the light includes different wavelengths or colors. In this manner a dimming device 126 when actuated changes the color of the lighting assembly from a first predetermined color to a second predetermined color. In one embodiment the first predetermined color is white and as the lighting assemblies are dimmed down the light output becomes red. In another embodiment the first predetermined color is white and the second predetermined color is blue. In yet another embodiment the first predetermined color is red and the second predetermined color is blue. While red and blue wavelengths are called out, other wavelengths, including but not limited to green wavelengths are contemplated by and do not fall outside the scope of this disclosure.

The lighting assemblies 38 are also spread out evenly across the facility 10, in one embodiment in a grid like manner, such that a generally evenly spread out intensity of light is provided on the avian. In this manner no change in light intensity is detected by the avian providing a calming condition to the avian. Thus stress on the avian is reduced providing a healthier avian that is less susceptible to diseases such as ulcers.

Thus, in operation the control system 118 is programmed to provide not only predetermined wavelengths or colors, in addition the timing device 124 sets predetermined intervals for each day. In particular, the control system 118 can provide 16 hours of white light during a day and then actuate the dimming device 126 to dim the lighting assemblies 38 to a red light for 8 hours. Then after the 8 hours, the dimming device 126 is actuated to again provide white light. The programming 122 can additionally be configured to then vary the predetermined durations of time. Thus, for a first time period, such as a day or week the control system 118 provides a predetermined interval of 16 hours of white light and 8 hours of red light. Then for a second time period, such as a next day or week, the predetermined interval can go to a different predetermined time interval, such as 14 hours of white light and 10 hours of red light. Then during a third time period the predetermined time intervals can be changed to provide 12 hours of white light and 12 hours of red, and so on, such that any predetermined levels can be accomplished by the lighting assemblies 14 in a given day. Thus any daily photoperiod and light spectrum desired by an end user can be provided.

In one embodiment the control system 118 is used on lighting assemblies 38 that are actuated to provide 14 hours of dark for the avian and 10 hours of light which is provided for a first week. Then every week the control system 118 reduces the amount of dark and increases the amount of light by an hour, such that in the second week 13 hours of dark is provided and 11 hours of light, in week 3 12 hours of dark and 12 hours of light, in week 4 11 hours of dark and 13 hours of white, in week 5 10 hours of dark and 14 hours of light, in week 6 9 hours of dark and 15 hours of light and finally in week 7 8 hours of dark and 16 hours of light.

Then, in this preferred embodiment in week 8, every day the dark and light predetermined periods are reversed back, such that on a first day 9 hours of dark is presented and 15 hours of light, on the second day 10 hours of dark and 14 hours of light and so on until 14 hours of dark and 10 hours of light is again provided. At this point again the control system steps down the amount of dark one week at a time such that in week 9 14 hours of dark and 10 hours of light is provided, in week 10 13 hours of dark and 11 hours of light is provided, in week 11 12 hours of dark and 12 hours of light is provided and so on until again 8 hours of dark is presented with 16 hours of light.

As a result of increasing the photoperiod over a seven week period avian are cued to a spring seasonality, which in nature results in the avian being at their most fertile condition and producing there highest concentration of seamen.

In addition to increasing predictability and optimizing artificial insemination sperm is simultaneously enhanced as a result of the use of the red wavelength of light. In particular, the avian contains one or more mitochondrion located between flagellar primordium (flagellum) and sperm nucleus. Mitochondrial energy levels as indicated by the amount of the adenosine triphosphate (ATP) within the mitochondria determine flagellar beating frequency and also time of beating, or motility.

Cytochrome C Oxidase is a photosensitive protein that is one of the four protein complexes in the outer mitochondria membrane. Specifically, cells in a redox (reduction-oxidation) state are more sensitive to light than those in a normal state and the voltage potential between the inner and outer mitochondrial membrane changes under photo-stimulation by far-red and infrared (IR) light. This change in voltage potential between the inner and outer mitochondrial membrane thus triggers ATP production. Specifically, Cytochrome C Oxidase has a copper core and the rest of four protein complexes involved in outer shell of the mitochondrion also contain metals.

Due to the redox state, there are a lot of ions present that is very similar to a photovoltaic cell. Therefore, by providing an external light source of right spectrum and frequency to mitochondria ATP, production is enhanced increasing sperm motility.

In one embodiment the spectrum is in the red spectrum of light or 620 nm-750 nm. In another embodiment the spectrum is more than 750 nm and in other embodiments the spectrum is less than 620 nm. Still, by selecting a predetermined spectrum, ATP production is enhanced and sperm motility enhanced, thus increasing conception for avian as compared to a similarly situated avian that had no light treatment been provided.

Similarly, when the sperm is in storage and being transported, whether within a cooled storage facility or during the thawing process, the use of lighting assemblies 38 that provide the red spectrum of light enhances the ATP production resulting in increasing the viability or life of the sperm without the use of a semen extender.

While described as providing the red spectrum of light before insemination, the red spectrum of light can be provided at any time, including after collection, during storage, during the thawing process or even after insemination. In particular, the red spectrum of light dose can be provided initially after collection and then after a predetermined amount of time when the mitochondria needs to be recharged and ATP production enhanced, a second or third dose can be delivered during storage or after insemination or other time thereafter to recharge or enhance ATP production. In this manner studies can be conducted to determine the period of time needed to recharge or enhance ATP production without allowing the sperm cell to expire such that no recharging can occur. Then doses of red light is timed to minimize the use of light and energy usage while maximizing the length of time sperm is viable.

In addition, individual cells producing ATP only need doses of light in small doses to produce ATP and exposing a cell to additional light often is unneeded or can be harmful as the cell is not allowed to complete production. Thus, providing pulsed light or predetermined periods of red light, or other wavelength of light, and darkness where the predetermined periods are between 0-5 ms can optimize the production of ATP.

In one embodiment the spectrum is provided by supplemental lighting used during the artificial insemination process to increase motility a predetermined amount of time, such as within one hour, of delivery to the semen to the avian. Therefore success in breeding in again enhanced.

In yet another embodiment flagellar beating is caused by voltage differential pulses caused by pulsed light. In this manner flagellar beating is caused directly by the pulsing light, again increasing motility and thus increasing the probability of breeding as compared to rates had no light treatment been provided.

With this said, just as red light can be used to increase ATP production and thus increase viability, motility, hatchability and otherwise, blue wavelength light (between 395 nm-450 nm) has an opposite effect on ATP production, causing the ATP production to cease. In this manner blue wavelength light can be used to control population to ensure the size of a flock is within the capability of a facility.

In a test conducted deep red wavelength light and royal blue light was used on sperm before insemination and the sperm itself was tested against a dark control. The test showed that the sperm with treatments of pulsed red light all were consistently more motile than the control while the treatments of pulsed royal blue where all consistently less motile than the control. Thus, the decay of the sperm under the pulsed red light decreased providing for a longer lasting sperm. By increasing the sperm life not only can lighting assemblies 38 having a red wavelength be used to supplement or enhance freezing techniques to prolong sperm life, but in addition, increases inception success. In particular an egg can develop in the ovarian tube for weeks meaning to ensure a successful insemination sperm needs to survive long enough to fertilize the egg. By increasing the ATP and thus the length of viability of the sperm you increase the probability that inception occurs.

Thus provided is a system and method that increases predictability and probability of breeding of avian as compared to the predictability and probability of breeding without use of the system and method. In particular a lighting regime and system provides periodic decreases in light over a period thus causing avian to perceive that a spring photoperiod is presented, providing higher probability of conception, but in addition, providing a cycle for the avian so that the time of conception becomes more predictable and better data can be provided. Further, by evenly distributing light, a calmer healthier avian is provided.

In another embodiment, the avian is provided a diet high in copper or nutrients that cause the avian or animal to produce increased levels of copper in the mitochondria to enhance ATP production by supplementing the Cytochrome C Oxidase with copper. Similarly diets high in zinc or other metals found in mitochondria or proteins within the mitochondria can be provided to supplement and enhance the use of light to cause a biochemical reaction within the mitochondria.

In addition, by using a predetermined wavelength of light, and in one embodiment in the 620 nm-750 nm range, physiologically the sperm viability for avian is also increased. In this manner the probability of successfully breeding of avian as compared to the probability of successfully breeding without use of the system and method is increased and can be better controlled. Also, previous costly methods of increasing viability of sperm can be avoided. Therefore, all of the stated problems are overcome.

What is claimed:

1. A method for increasing the viability of sperm, comprising:
    irradiating sperm with light having a spectrum substantially concentrated within a narrow range of wavelength for a predetermined period of time and selecting the narrow range of wavelength for the spectrum of light irradiating the sperm to increase the motility of the sperm; and
    pulsing the light for periods of light and darkness.

2. The method of claim 1 further comprising shielding the sperm from light having a spectrum substantially outside the narrow range of wavelengths.

3. The method of claim 1 wherein the narrow range of wavelength is selected to be between 620 nm and 780 nm.

4. The method of claim 3 wherein the narrow range of wavelength is selected to be between 620 nm and 750 nm.

5. The method of claim 1 wherein the light is generated by a light emitting diode.

6. The method of claim 5 wherein the light is pulsed for a period of time between 0 ms and 5 ms.

7. The method of claim 1 wherein the light is pulsed at a rate proportional to the flagellar beating frequency of the sperm.

8. The method of claim 7 wherein the light is pulsed at the flagellar beating frequency of the sperm.

9. The method of claim 1 wherein the sperm is selected from a group consisting of: horse, swine, bovine, sheep, goat, fish, shrimp, and avian sperm.

10. The method of claim 1 wherein the sperm is turkey sperm.

11. A method for increasing the viability of sperm, comprising:
    irradiating sperm with light having a spectrum substantially concentrated within a narrow range of wavelength for a predetermined period of time, and selecting the narrow range of wavelength for the spectrum of light irradiating the sperm to increase the motility of the sperm; and
    delivering the sperm to an egg within one hour of the irradiating.

12. The method of claim 11 wherein the narrow range of wavelength is selected to be between 620 nm and 780 nm.

13. The method of claim 11 wherein the narrow range of wavelength is selected to be between 620 nm and 750 nm.

14. The method of claim 11 wherein the sperm is selected from a group consisting of: horse, swine, bovine, sheep, goat, fish, shrimp, and avian sperm.

15. The method of claim 11 wherein the light is generated by a light emitting diode.

16. A method for increasing the viability of sperm, comprising:
    irradiating sperm with light having a spectrum substantially concentrated within a narrow range of wavelength for a predetermined period of time and selecting the narrow range of wavelength for the spectrum of light irradiating the sperm to increase the motility of the sperm;
    wherein the sperm is avian.

17. The method of claim 16 wherein the sperm is turkey sperm.

18. The method of claim 16 wherein the narrow range of wavelength is selected to be between 620 nm and 780 nm.

19. The method of claim 16 wherein the narrow range of wavelength is selected to be between 620 nm and 750 nm.

20. The method of claim 16 wherein the light is generated by a light emitting diode.

\* \* \* \* \*